(12) United States Patent
Uwaydah (10) Patent No.: US 6,776,781 B1
(45) Date of Patent: Aug. 17, 2004

(54) SPINAL-COLUMN BUTTRESS PLATE ASSEMBLY AND METHOD FOR ATTACHMENT

(75) Inventor: Munir M. Uwaydah, Monroe, MI (US)

(73) Assignee: Farihan Renno, Redondo Beach, CA (US)

( * ) Notice: Subject to any disclaimer, the term of this patent is extended or adjusted under 35 U.S.C. 154(b) by 0 days.

(21) Appl. No.: 09/672,552

(22) Filed: Sep. 28, 2000

(51) Int. Cl.$^7$ .............................................. A61B 17/58
(52) U.S. Cl. .......................................... 606/69; 606/61
(58) Field of Search ...................... 606/60, 61, 69–71, 606/72, 73

(56) References Cited

U.S. PATENT DOCUMENTS

| | | | |
|---|---|---|---|
| 5,209,751 A | * 5/1993 | Farris et al. .................. | 606/61 |
| 5,324,290 A | * 6/1994 | Zdeblick et al. ............... | 606/61 |
| 5,344,421 A | * 9/1994 | Crook .......................... | 606/61 |
| 5,364,399 A | 11/1994 | Lowery et al. ................ | 606/69 |
| 5,395,372 A | * 3/1995 | Holt et al. .................... | 606/61 |
| 5,578,034 A | 11/1996 | Estes ............................ | 606/61 |
| 5,676,666 A | * 10/1997 | Oxland et al. ................ | 606/61 |
| 5,681,311 A | 10/1997 | Foley et al. .................. | 606/61 |
| 5,766,254 A | 6/1998 | Gelbard ........................ | 623/17 |
| 5,843,082 A | 12/1998 | Yuan et al. .................... | 606/61 |
| 5,899,904 A | * 5/1999 | Errico et al. .................. | 606/61 |
| 5,904,683 A | 5/1999 | Pohndorf et al. ............. | 606/61 |
| 5,961,519 A | * 10/1999 | Bruce et al. ................. | 606/69 |
| 6,017,345 A | 1/2000 | Richelsoph .................. | 606/70 |
| 6,030,389 A | 2/2000 | Wagner et al. ................ | 606/71 |

FOREIGN PATENT DOCUMENTS

CH    WO 88/03781    * 6/1988    .................. 606/69

* cited by examiner

Primary Examiner—Kevin Shaver
Assistant Examiner—Michael B. Priddy (57) ABSTRACT

A spinal-column (e.g., cervical-column) buttress plate assembly and method for attaching together first and second vertebral bodies of a spinal column (e.g., cervical column) of a medical patient. Bone screws are inserted into the vertebral bodies at optimum locations on the vertebral bodies. A buttress plate having an elongated slot is placed on the vertebral bodies so that the heads of the bone screws are positioned in the elongated slot. Inner screws are threaded into the bone screws to expand their heads against the opposing edges of the elongated slot thereby attaching the buttress plate to the vertebral bodies.

36 Claims, 5 Drawing Sheets

FIG.2

SPINAL-COLUMN BUTTRESS PLATE ASSEMBLY AND METHOD FOR ATTACHMENT

BACKGROUND OF THE INVENTION

The present invention relates generally to medical apparatus and procedures, and more particularly to apparatus and a method which attaches a spinal-column buttress plate to two vertebral bodies of a spinal column of a medical patient.

Conventional medical procedures include attaching together (sometimes called fusing) first and second vertebral bodies of a spinal column (such as adjacent first and second cervical vertebral bodies of the cervical column portion of the spinal column) of a medical patient. A spinal-vertebral buttress plate (such as a cervical-vertebral buttress plate) of appropriate length is obtained. The buttress plate is positioned on the anterior side of the first and second vertebral bodies. The buttress plate comes with pre-drilled holes. Using first and second holes, of the positioned buttress plate, which are aligned over the first vertebral body, first and second starter holes are marked and drilled on the anterior cortex of the first vertebral body. Using third and fourth holes, of the positioned buttress plate, which is aligned over the second vertebral body, third and fourth starter holes are marked and drilled on the anterior cortex of the second vertebral body. A first bone screw is inserted in the first hole and a second bone screw is inserted in the second hole of the buttress plate and threaded into the corresponding starter hole in the anterior cortex of the first vertebral body, and a third bone screw is inserted in the third hole and a fourth bone screw is inserted in the fourth hole of the buttress plate and threaded into the corresponding starter hole in the anterior cortex of the second vertebral body. With the four bone screws securing the spinal-column buttress plate to the first and second vertebral bodies, the first and second vertebral bodies are thereby attached together (or fused) preventing their relative movement. Attachment problems arise when the pre-drilled holes of the spinal-column buttress plate are only alignable over a non-optimum area of the first and/or second vertebral body.

What is needed is a spinal-column buttress plate assembly (such as a cervical-column buttress plate assembly) and a method for attachment which provides better attachment of the spinal-column (e.g., cervical-column) buttress plate to the first and second vertebral bodies (e.g., the first and second cervical vertebral bodies.

SUMMARY OF THE INVENTION

A first expression of a preferred embodiment of the invention is for a cervical-column buttress plate assembly for fusing together first and second cervical vertebral bodies of a cervical column of a medical patient. The buttress plate assembly includes a first cervical-vertebral buttress plate, a first screw assembly, and a second screw assembly. The cervical-vertebral buttress plate has an elongated slot with opposing and serrated edges. The first screw assembly includes a first bone screw and a first inner screw. The first bone screw has an internally-threaded hole, has an externally-threaded shaft which is threadably insertable into the first cervical vertebral body of the cervical column of the medical patient and which has an expandable tip, and has an expandable head which is attached to the shaft and which has external teeth. The second screw assembly has a second bone screw and a second inner screw. The second bone screw has an internally-threaded hole, has an externally-threaded shaft which is threadably insertable into the second cervical vertebral body of the cervical column of the medical patient and which has an expandable tip, and has an expandable head which is attached to the shaft and which has external teeth. The first and second inner screws are engageable, respectively, in the internally-threaded holes of the first and second bone screws to expand the tips of the first and second bone screws against the first and second cervical vertebral bodies and to expand the heads of the first and second bone screws to engage the external teeth of the heads of the first and second bone screws against the opposing and serrated edges of the elongated slot of the buttress plate after the elongated slot of the buttress plate has been disposed to enclose the heads of the first and second bone screws after the first and second bone screws have been threadably inserted into the first and second vertebral bodies.

A second expression of a preferred embodiment of the invention is for a spinal-column buttress plate assembly for attaching together first and second vertebral bodies of a spinal column of a medical patient. The buttress plate assembly includes a spinal-vertebral buttress plate, a first screw assembly, and a second screw assembly. The buttress plate has an elongated slot with opposing edges. The first screw assembly includes a first bone screw and a first inner screw. The first bone screw has an internally-threaded hole, has a shaft which is insertable into the first vertebral body of the spinal column of the medical patient, and has an expandable head which is attached to the shaft and which has a first unexpanded state and a first expanded state. The head of the first bone screw is small enough to pass through the elongated slot in the first unexpanded state but not in the first expanded state. The second screw assembly includes a second bone screw and a second inner screw. The second bone screw has an internally-threaded hole, has a shaft which is insertable into the second vertebral body of the spinal column of the medical patient, and has an expandable head which is attached to the shaft and which has a second unexpanded state and a second expanded state. The head of the second bone screw is small enough to pass through the elongated slot in the second unexpanded state but not in the second expanded state. The first and second inner screws are engageable, respectively, in the internally-threaded holes of the first and second bone screws to expand the heads of the first and second bone screws to engage the heads of the first and second bone screws against the opposing edges of the elongated slot of the buttress plate after the elongated slot of the buttress plate has been disposed to enclose the heads of the first and second bone screws after the first and second bone screws have been inserted into the first and second vertebral bodies.

An alternate preferred embodiment is identical to the previously-described second expression of the preferred embodiment except that the buttress plate has first and second elongated slots with the first bone screw associated with the first elongated slot and with the second bone screw associated with the second elongated slot.

A first expression of a method of the invention is for fusing together first and second vertebral bodies of a spinal column of a medical patient and includes steps a) through h). Step a) includes obtaining first and second bone screws each having an internally-threaded hole, each having a shaft with an expandable tip, and each having an expandable head attached to the shaft and having external teeth. Step b) includes obtaining first and second inner screws engageable, respectively, with the internally-threaded holes of the first and second bone screws to expand the tips and the heads of the first and second bone screws. Step c) includes obtaining a buttress plate having an elongated slot with opposing and serrated edges. Step d) includes inserting the first bone screw into the first vertebral body of the spinal column of the medical patient with the head of the first bone screw protruding above the first vertebral body. Step e) includes inserting the second bone screw into the second vertebral body of the spinal column of the medical patient with the head of the second bone screw protruding above the second vertebral body. Step f) includes placing the buttress plate on the first and second vertebral bodies with the heads of the first and second bone screws disposed in the elongated slot of the buttress plate. Step g) includes threading the first inner screw into the internally-threaded hole of the first bone screw expanding the tip of the first bone screw against the first vertebral body and expanding the head of the first bone screw to engage the external teeth of the head of the first bone screw against the opposing and serrated edges of the elongated slot of the buttress plate. Step h) includes threading the second inner screw into the internally-threaded hole of the second bone screw expanding the tip of the second bone screw against the second vertebral body and expanding the head of the second bone screw to engage the external teeth of the head of the second bone screw against the opposing and serrated edges of the elongated slot of the buttress plate.

A second expression of a method of the invention is for attaching together first and second vertebral bodies of a spinal column of a medical patient and includes steps a) through h). Step a) includes obtaining first and second bone screws each having an internally-threaded hole, each having a shaft, and each having an expandable head attached to the shaft. Step b) includes obtaining first and second inner screws engageable, respectively, with the internally-threaded holes of the first and second bone screws to expand the heads of the first and second bone screws. Step c) includes obtaining a buttress plate having an elongated slot with opposing edges. Step d) includes inserting the first bone screw into the first vertebral body of the spinal column of the medical patient with the head of the first bone screw protruding above the first vertebral body. Step e) includes inserting the second bone screw into the second vertebral body of the spinal column of the medical patient with the head of the second bone screw protruding above the second vertebral body. Step f) includes placing the buttress plate on the first and second vertebral bodies with the heads of the first and second bone screws disposed in the elongated slot of the buttress plate. Step g) includes threading the first inner screw into the internally-threaded hole of the first bone screw expanding the head of the first bone screw to engage the head of the first bone screw against the opposing edges of the elongated slot of the buttress plate. Step h) includes threading the second inner screw into the internally-threaded hole of the second bone screw expanding the head of the second bone screw to engage the head of the second bone screw against the opposing edges of the elongated slot of the buttress plate.

An alternate second expression of a method of the invention is identical to the previously-described second expression of a method of the invention except that the buttress plate has first and second elongated slots with the first bone screw associated with the first elongated slot and with the second bone screw associated with the second elongated slot.

A third expression of a method of the invention is for attaching together first and second vertebral bodies of a spinal column of a medical patient and includes steps a) through e). Step a) includes obtaining first and second bone screws. Step b) includes obtaining a buttress plate. Step c) includes inserting the first bone screw into the first vertebral body of the spinal column of the medical patient. Step d) includes inserting the second bone screw into the second vertebral body of the spinal column of the medical patient. Step e) includes attaching the buttress plate to the first and second bone screws after performing steps a) through d).

Several benefits and advantages are derived from the invention. The apparatus and method of the invention allows a physician to choose an optimum location for the first bone screw on the first vertebral body (e.g., on the first cervical vertebral body) and to choose an optimum location for the second bone screw on the second vertebral body (e.g., on the second cervical vertebral body) for maximum attachment strength and mechanical stability. This is accomplished by first installing the bone screws on the vertebral bodies and then securing the buttress plate to the installed bone screws. In comparison, the prior art forces the physician to use pre-drilled holes in the buttress plate which often provide less than optimum attachment locations (providing less attachment strength and less mechanical stability) for the bone screws to be installed in the vertebral bodies.

DETAILED DESCRIPTION

Figure 1:
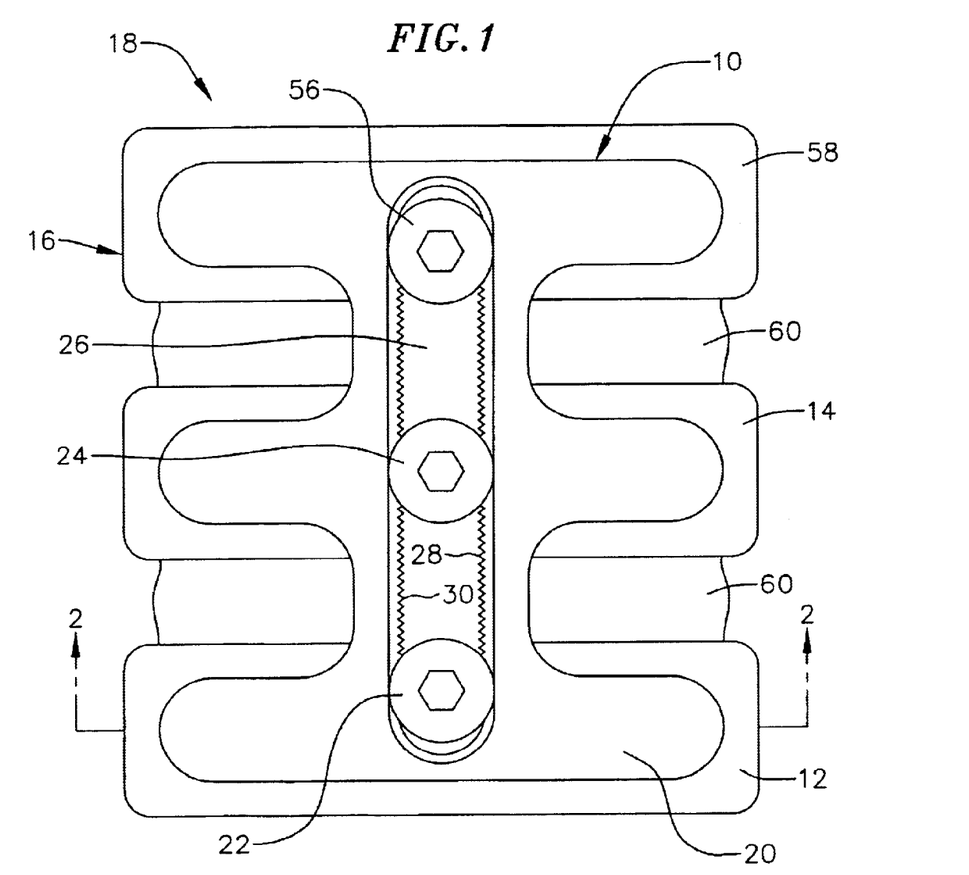
FIG. 1 is a schematic, top planar view a preferred embodiment of the buttress plate assembly of the invention (showing a buttress plate and three screw assemblies) attached to three vertebral bodies of a spinal column of a medical patient.

A preferred embodiment of the invention, shown in FIGS. 1–8, is for a spinal-column buttress plate assembly 10 for attaching together first and second vertebral bodies 12 and 14 of a spinal column 16 of a medical patient 18 (only a portion of the spinal column of whom is shown in FIG. 1). Preferably, the spinal column 16 is a cervical column, the first and second vertebral bodies 12 and 14 are first and second cervical vertebral bodies, the spinal-column buttress plate assembly 10 is a cervical-column buttress plate assembly, and the spinal-column buttress plate assembly 10 is for fusing together the first and second cervical vertebral bodies of the cervical column of the medical patient. Preferably, the cervical-column buttress plate assembly is an anterior cervical-column buttress plate assembly. In other medical procedures, the first and second vertebral bodies 12 and 14 are vertebral bodies of an upper back portion and/or a lower back portion of the spinal column. Preferably the medical patient is a person, although the buttress plate assembly 10 of the invention is applicable to animals having spinal columns with vertebral bodies. It is noted that the terminology "first (or second) vertebral body" means a vertebral body (also known as a vertebral level) and is not limited to a specific vertebral body medically known as the first (or second) vertebral body or level.

The spinal-column buttress plate assembly 10 of FIGS. 1–8 includes a spinal-vertebral buttress plate 20, a first screw assembly 22, and a second screw assembly 24. Preferably, the spinal-vertebral buttress plate 20 is a cervical-vertebral buttress plate. The buttress plate 20 has an elongated (and preferably longitudinal) slot 26 with opposing edges 28 and 30, and preferably the opposing edges 28 and 30 are opposing and serrated edges. In a preferred construction, the buttress plate 20 comprises (and preferably consists essentially of, and more preferably consists of) titanium or a titanium alloy.

The first screw assembly 22 includes a first bone screw 32 and a first inner screw 34 having threads which are preferably tapered. The first bone screw 32 has an internally-threaded hole 36 which preferably is a through hole coaxially aligned with the longitudinal axis of the first bone screw 32 (not to be confused with the longitudinal axis of the buttress plate). The first bone screw 32 also has a shaft 38 which is insertable into the first vertebral body 12 of the spinal column 16 of the medical patient 18. Preferably, the shaft 38 is an externally-threaded shaft which is threadably insertable into the first vertebral body 12. It is noted that the terminology "bone screw" includes any elongated member, threaded or non-threaded, which is securable within a bone. Typically, a starter hole is made by an awl, and the first bone screw 32 is inserted into the starter hole. The first bone screw 32 additional has an expandable head 40 attached to the shaft 38. The expandable head 40 has a first unexpanded state and a first expanded state. The head 40 of the first bone screw 32 is small enough to pass through the elongated slot 26 in the first unexpanded state but not in the first expanded state. In one design, the head 40 has a longitudinal slit 42 which allows head expansion. Preferably, the shaft 38 has an expandable tip 44. In one design, the tip 44 has a longitudinal slit 46 which allows tip expansion. Preferably, the expandable head 40 has external teeth 48.

The second screw assembly 24, shown in FIG. 1, is substantially identical to the first screw assembly 22 shown in detail in FIGS. 2 and 5–8, and therefore details of the second screw assembly 24 are not separately shown. The second screw assembly 24 includes a second bone screw substantially identical to the first bone screw 32 and a second inner screw substantially identical to the first inner screw 34. The second bone screw has an internally-threaded hole which preferably is a through hole coaxially aligned with the longitudinal axis of the second bone screw (not to be confused with the longitudinal axis of the buttress plate). The second bone screw also has a shaft which is insertable into the second vertebral body 14 of the spinal column 16 of the medical patient 18. Preferably, the shaft is an externally-threaded shaft which is threadably insertable into the second vertebral body 14. It is noted that the terminology "bone screw" includes any elongated member, threaded or non-threaded, which is securable within a bone. Typically, a starter hole is made by an awl, and the second bone screw is inserted into the starter hole. The second bone screw additional has an expandable head attached to the shaft. The expandable head has a second unexpanded state and a second expanded state. The head of the second bone screw is small enough to pass through the elongated slot in the second unexpanded state but not in the second expanded state. In one design, the head has a longitudinal slit which allows head expansion. Preferably, the shaft has an expandable tip. In one design, the tip has a longitudinal slit which allows tip expansion. Preferably, the expandable head has external teeth.

The first and second inner screws 34 are engageable, respectively, in the internally-threaded holes 36 of the first and second bone screws 32 to expand the heads 40 of the first and second bone screws 32 to engage the heads 40 of the first and second bone screws 32 against the opposing edges 28 and 30 of the buttress plate 20 after the elongated slot 26 of the buttress plate has been disposed to enclose the heads 40 of the first and second bone screws 32 after the first and second bone screws 32 have been inserted into the first and second vertebral bodies 12 and 14. Preferably, the first and second inner screws 34 are engageable, respectively, in the internally-threaded holes 36 of the first and second bone screws 32 to expand the tips 44 of the first and second bone screws against the first and second cervical vertebral bodies and to expand the heads 40 of the first and second bone screws to engage the external teeth 48 of the heads of the first and second bone screws against the opposing and serrated edges of the buttress plate 20 after the elongated slot of the buttress plate has been disposed to enclose the heads of the first and second bone screws after the first and second bone screws have been threadably inserted into the first and second vertebral bodies. In one example, the heads 40 have different textured outer surfaces (instead of the preferred longitudinally-extending external teeth) and the opposing edges 28 and 30 have different textured surfaces (instead of the preferred serrations) to have the heads better grip the opposing edges.

Figure 2:
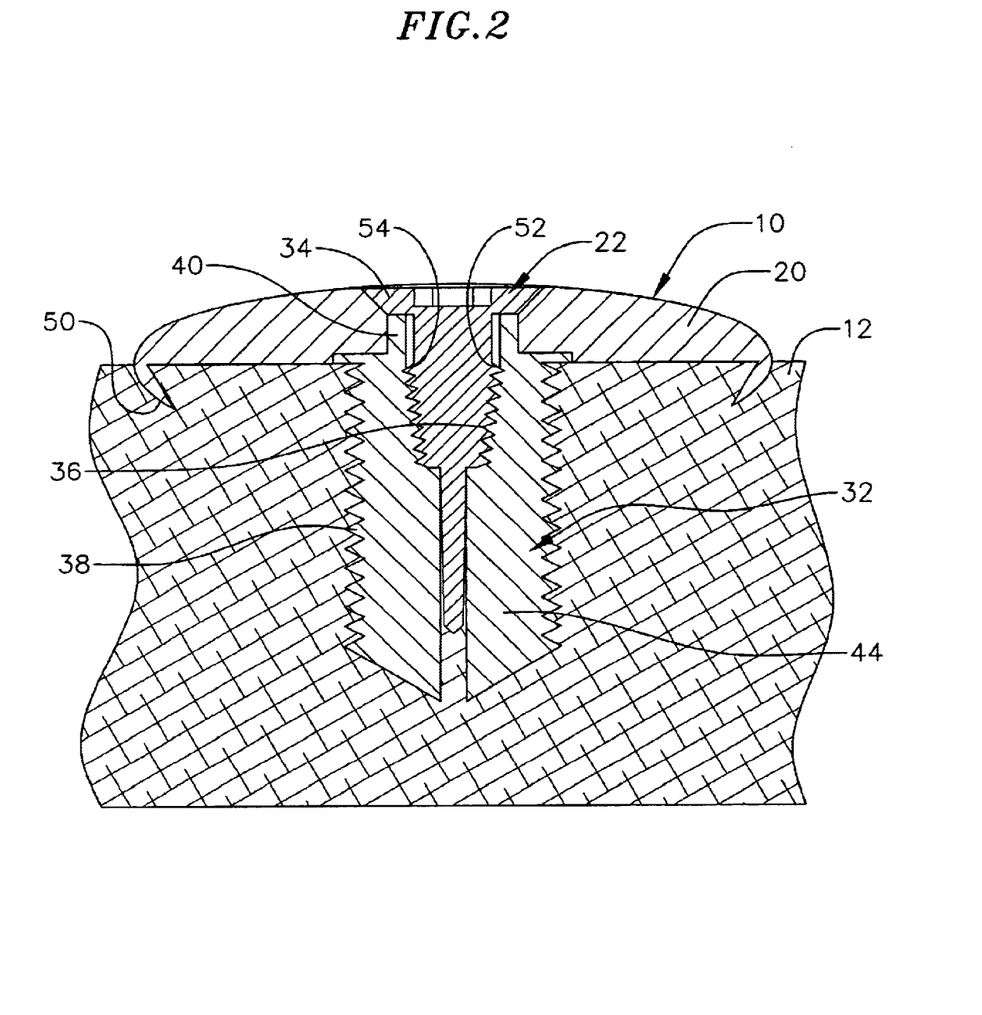
FIG. 2 is a cross-sectional view of the buttress plate assembly and one of the vertebral bodies of FIG. 1 taken along lines 2—2 in FIG. 1.
Figure 3:
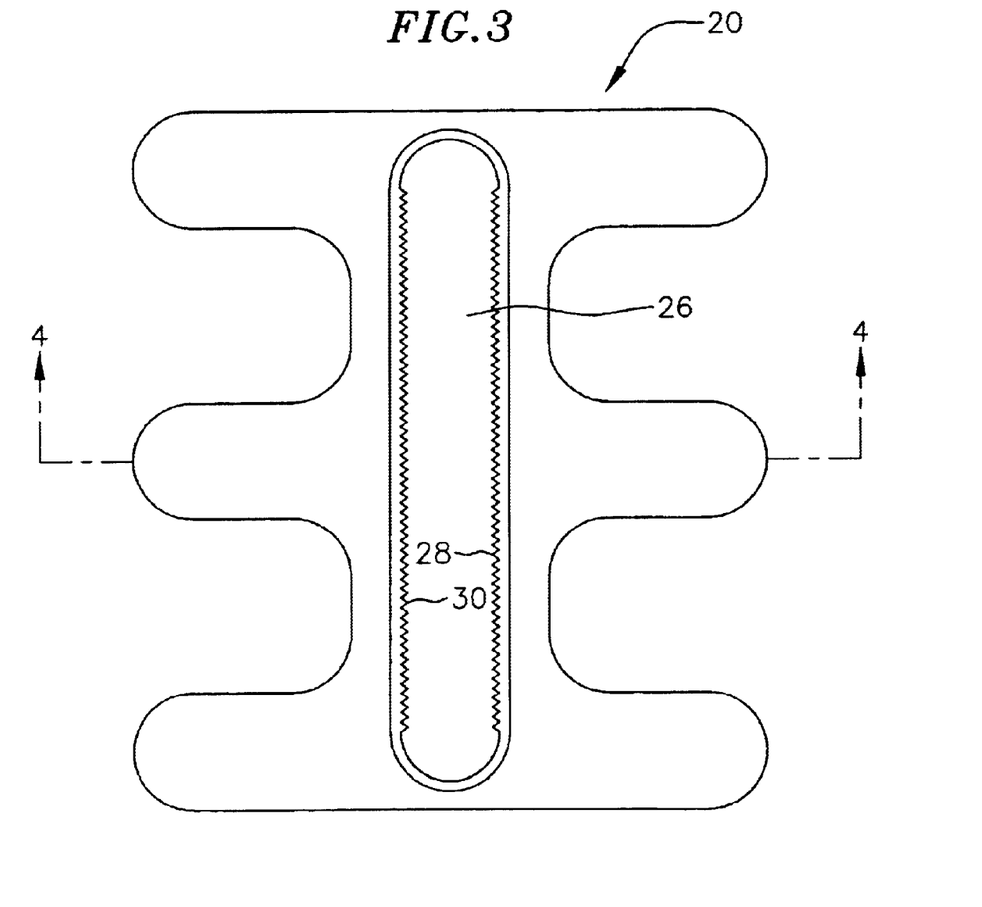
FIG. 3 is a schematic, top planar view of the buttress plate portion of the buttress plate assembly of FIGS. 1 and 2.
Figure 4:
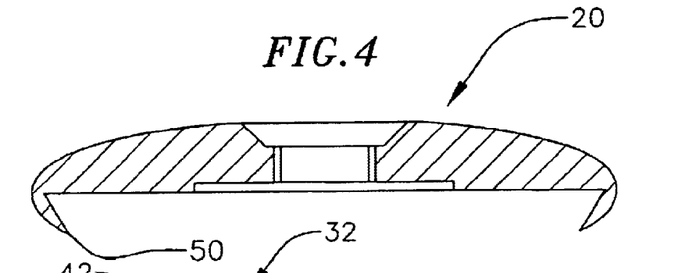
FIG. 4 is a cross-sectional view of the buttress plate of FIG. 3 taken along lines 4—4 in FIG. 3.
Figure 5:
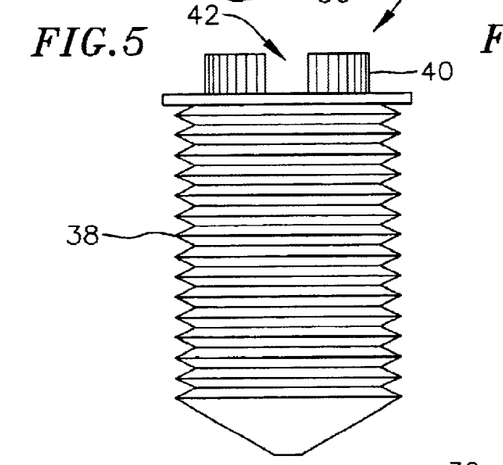
FIG. 5 is a front elevational view of a bone screw portion of a first screw assembly of FIGS. 1 and 2.
Figure 6:
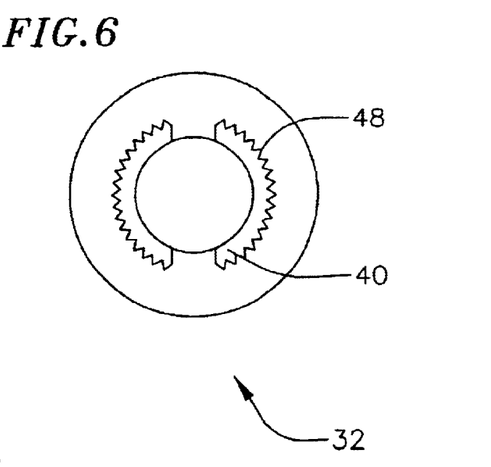
FIG. 6 is a top planar view of the bone screw of FIG. 5.
Figures 7, 8:
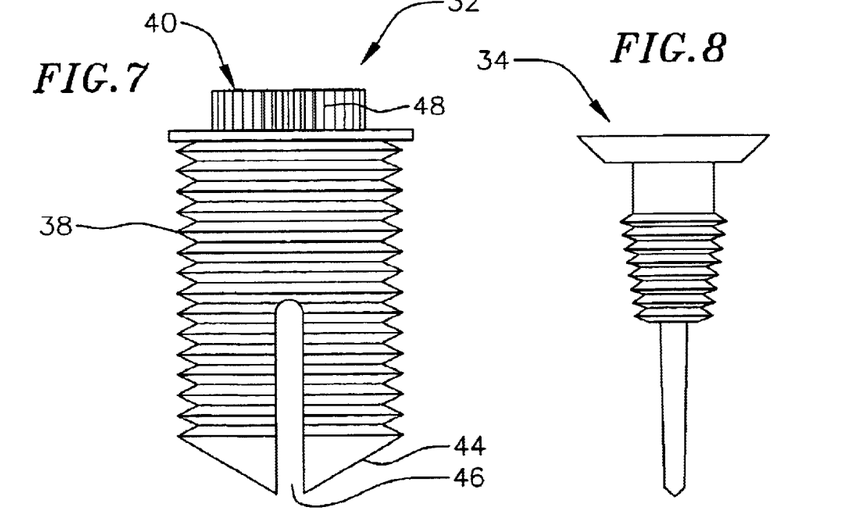
FIG. 7 is a side elevational view of the bone screw of FIG. 5.
FIG. 8 is a front elevational view of an inner screw portion of the first screw assembly of FIGS. 1.

In a preferred construction, the buttress plate 20 includes claws (i.e., bone claws) 50 engageable with the first and second vertebral bodies 12 and 14. The claws 50 provide the buttress plate 20 with a better grip on the first and second vertebral bodies 12 and 14. The bone claws are located along the prominent edges of the inferior side of the buttress plate 20. In an example, the first bone screw 32 includes first means 52 for trapping the first inner screw 34 when the first inner screw 34 is fully engaged in the internally-threaded hole 36 of the first bone screw 32, and wherein the second bone screw includes second means for trapping the second inner screw when the second inner screw is fully engaged in the internally-threaded hole of the second bone screw. This will prevent the first inner screw 34 from backing out of the first bone screw 32. Preferably, the second means is substantially identical to the first means 52, and the first means includes a lip 54 which is attached to, or a monolithic portion of, the shaft 38. Other means include conventional anti-rotation features employed with, or on, conventional bolts and screws, as is known to those skilled in the art. For example, in one variation (not shown), a screw cap (which either is separate from or attached to the first inner screw) further secures the first inner screw to the first bone screw preventing screw back out. In a preferred design, the head 40 of the first bone screw 32 has a substantially rectangular shape, and the head of the second bone screw has a substantially rectangular shape. This will provide a better grip for the expansion of the head 40 against the opposing edges 28 and 30.

The spinal-column buttress plate assembly 10 of FIG. 1 includes a third screw assembly 56, substantially identical to the first screw assembly 22, whereby the spinal-vertebral buttress plate 20 is also attached to a third vertebral body 58 of the spinal column 16. Different buttress plates may span two or more vertebral bodies depending on the needs of a particular medical application. Preferably, the buttress plate 20 is narrow-waisted over soft tissue regions 60 between the vertebral bodies 12, 14, and 58, as seen in FIG. 1. Each narrow-waisted region of the buttress plate 20 provides a bend zone for inter-operative modification, as can be appreciated by the artisan. Preferably, there is one bone screw for each involved vertebral level (i.e., body).

Figure 9:
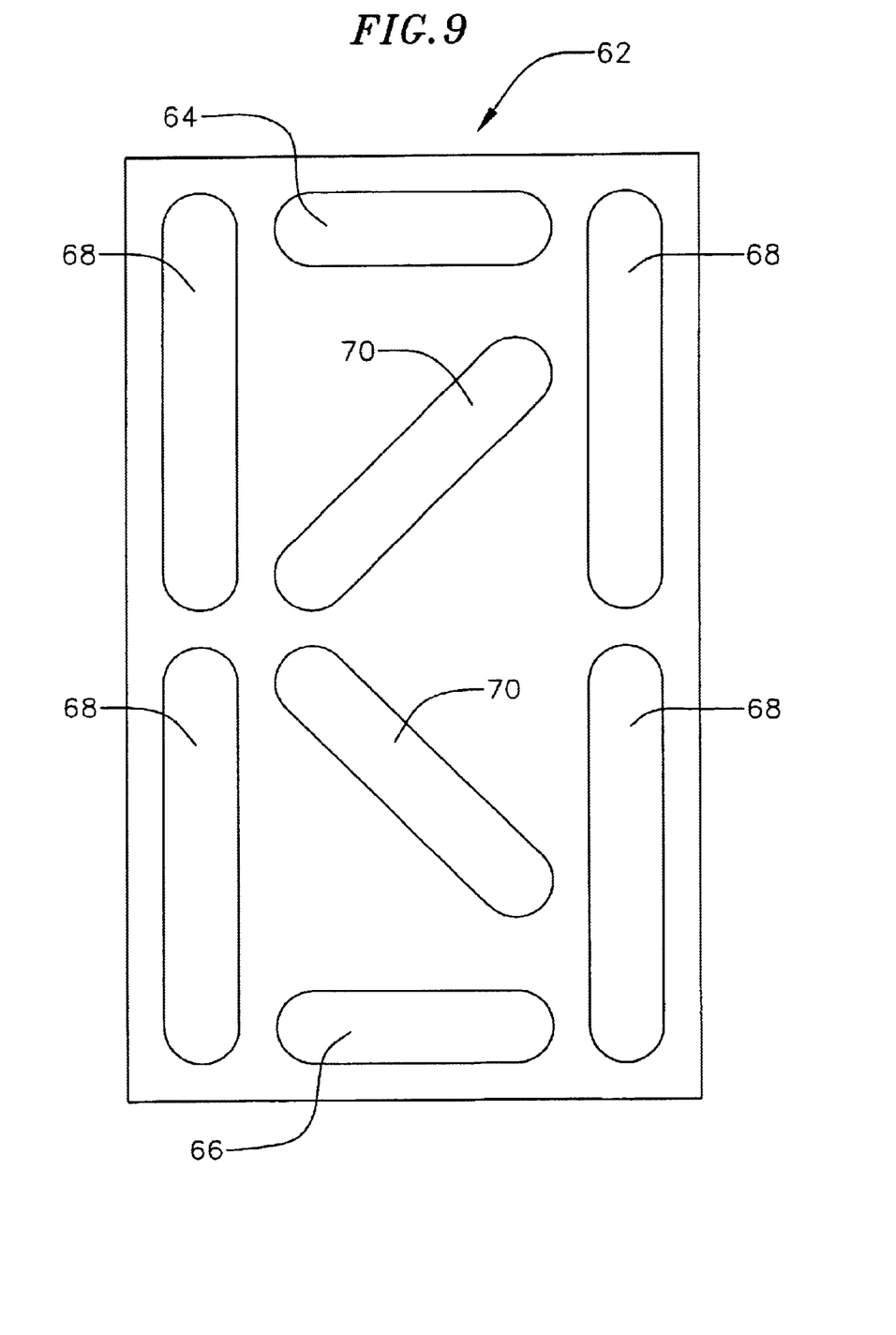
FIG. 9 is a schematic, top planar view of an alternate preferred embodiment of a buttress plate showing multiple elongated slots having various orientations.

An alternate embodiment of the buttress plate 62 is shown in FIG. 9 as including a first elongated slot 64, a second elongated slot 66, and additional elongated slots 68 and 70. Here, the head 40 of the first bone screw 32 is small enough to pass through the first elongated slot 64 in the first unexpanded state but not in the first expanded state, and the head of the second bone screw is small enough to pass through the second elongated slot 66 in the second unexpanded state but not in the second expanded state. The first elongated slot 64 is disposed to enclose the head 40 of the first bone screw 32, and the second elongated slot 66 is disposed to enclose the head of the second bone screw after the first bone screw 32 has been inserted into the first vertebral body 12 and the second bone screw has been inserted into the second vertebral body 14. It is noted that the first and second elongated slots 64 and 66 are horizontal slots, but that other applications require that the bone screws be engaged in longitudinal or oblique elongated slots 68 and 70 or in any combination of arbitrarily-aligned elongated slots and/or arbitrarily-located holes.

An example of a buttress plate 20 for cervical use is a buttress plate having rounded edges, having a length sufficient to span the required number of vertebral bodies to be fused, having a thickness of substantially 3 mm, having a width of substantially 18 mm over a vertebral body, having a width of substantially 10 mm over a soft tissue region, having a slot substantially 25 mm long and 4 mm wide with a substantially 1 mm wide and 1 mm deep chamfered perimeter extension. The chamfered perimeter extension allows the first inner screw 34 to sit flush with the surface of the buttress plate 20, as seen in FIG. 2. An example of a first bone screw 32 is a bone screw having a length of between substantially 12 and 16 mm, having a diameter of substantially 5 mm which will be positioned perpendicular to the anterior cortex and along the cephalo-caudal midline of each involved vertebral body. A typical use is to install the buttress plate after a graft to a soft tissue region so that the installed buttress plate provides intervertebral graft stabilization and fixation of the anterior cervical column. Preferably, a conventional-design adjustable-depth driver is used to insert the first bone screw 32 which prevents the first bone screw 32 from being driven beyond the proper depth into the first vertebral body 12. Preferably, the buttress plate 20 has an overall lordotic curve in the widthwise direction to match the curve of a vertebral body.

A first preferred method of the invention is for fusing together first and second vertebral bodies 12 and 14 of a spinal column 16 of a medical patient 18, and the method includes steps a) through h). Step a) includes obtaining first and second bone screws 32 each having an internally-threaded hole 36, each having a shaft 38 with an expandable tip 44, and each having an expandable head 40 attached to the shaft 38 and having external teeth 48. Step b) includes obtaining first and second inner screws 34 engageable, respectively, with the internally-threaded holes 36 of the first and second bone screws 32 to expand the tips 44 and the heads 40 of the first and second bone screws 32. Step c) includes obtaining a buttress plate 20 having an elongated slot 26 with opposing and serrated edges. Step d) includes inserting the first bone screw 32 into the first vertebral body 12 of the spinal column 16 of the medical patient 18 with the head 40 of the first bone screw 32 protruding above the first vertebral body 12. Step e) includes inserting the second bone screw into the second vertebral body 14 of the spinal column of the medical patient with the head of the second bone screw protruding above the second vertebral body. Step f) includes placing the buttress plate 20 on the first and second vertebral bodies 12 and 14 (with or without an intervening layer of something else) with the heads 40 of the first and second bone screws 32 disposed in the elongated slot 26 of the buttress plate 20. Step g) includes threading the first inner screw 34 into the internally-threaded hole 36 of the first bone screw 32 expanding the tip 44 of the first bone screw 32 against the first vertebral body 12 and expanding the head 40 of the first bone screw 32 to engage the external teeth 48 of the head 40 of the first bone screw 32 against the opposing and serrated edges of the elongated slot 26 of the buttress plate 20. Step h) includes threading the second inner screw into the internally-threaded hole of the second bone screw expanding the tip of the second bone screw against the second vertebral body 14 and expanding the head of the second bone screw to engage the external teeth of the head of the second bone screw against the opposing and serrated edges of the buttress plate.

A second preferred method of the invention is for attaching together first and second vertebral bodies 12 and 14 of a spinal column 16 of a medical patient 18, and the method includes steps a) through h) Step a) includes obtaining first and second bone screws 32 each having an internally-threaded hole 36, each having a shaft 38, and each having an expandable head 40 attached to the shaft 38. Step b) includes obtaining first and second inner screws 34 engageable, respectively, with the internally-threaded holes 36 of the first and second bone screws 32 to expand the heads 40 of the first and second bone screws. Step c) includes obtaining a buttress plate 20 having an elongated slot 26 with opposing edges 28 and 30. Step d) includes inserting the first bone screw 32 into the first vertebral body 12 of the spinal column 16 of the medical patient 18 with the head 40 of the first bone screw 32 protruding above the first vertebral body 12. Step e) includes inserting the second bone screw into the second vertebral body 14 of the spinal column of the medical patient with the head of the second bone screw protruding above the second vertebral body. Step f) includes placing the buttress plate 20 on the first and second vertebral bodies 12 and 14 (with or without an intervening layer of something else) with the heads 40 of the first and second bone screws 32 disposed in the elongated slot 26 of the buttress plate 20. Step g) includes threading the first inner screw 34 into the internally-threaded hole 36 of the first bone screw 32 expanding the head 40 of the first bone screw 32 to engage the head 40 of the first bone screw 32 against the opposing edges 28 and 30 of the elongated slot 26 of the buttress plate 20. Step h) includes threading the second inner screw into the internally-threaded hole of the second bone screw expanding the head of the second bone screw to engage the head of the second bone screw against the opposing edges of the elongated slot of the buttress plate.

In an alternate method, the buttress plate 62 has first and second elongated slots 64 and 66, and step f) places the buttress plate 62 so that the first bone screw 32 is disposed in the first elongated slot 64 and the second bone screw is disposed in the second elongated slot 66.

In the first and second preferred methods of the invention, preferably, the first and second vertebral bodies 12 and 14 are adjacent first and second vertebral bodies of the spinal column such as adjacent first and second cervical vertebral bodies of the spinal column. In these two methods, preferably step d) inserts the first bone screw 32 into the anterior cortex of the first (e.g., cervical) vertebral. body 12, and step e) inserts the second bone screw into the anterior cortex of the second (e.g., cervical) vertebral body. Also in these two methods, preferably step d) inserts the first bone screw 32 into the first (e.g., cervical) vertebral body 12 along the midline of the first (e.g., cervical) vertebral body 12, and wherein step e) inserts the second bone screw into the second (e.g., cervical) vertebral body 14 along the midline of the second (e.g., cervical) vertebral body. It is preferred in these two methods that the buttress plate 20 has claws 50, and that step f) includes tamping down the buttress plate 20 to engage the claws 50 into the anterior cortex of the first and second (e.g., cervical) vertebral bodies 12 and 14.

A third preferred method of the invention is for attaching together first and second vertebral bodies 12 and 14 of a spinal column 16 of a medical patient 18, and the method includes steps a) through e). Step a) includes obtaining first and second bone screws each having a shaft. Step b) includes obtaining a buttress plate. Step c) includes inserting the first bone screw into the first vertebral body of the spinal column of the medical patient. Step d) includes inserting the second bone screw into the second vertebral body of the spinal column of the medical patient. Step e) includes attaching the buttress plate to the first and second bone screws after performing steps a) through d).

In an example of a medical procedure utilizing a preferred method of the invention, the anterior cervical-column buttress plate is installed following a graft placement to a soft tissue region. The anterior aspect of a vertebral body is prepared by removing soft tissue and prominent osteophytes. The midline portion of the vertebral body is identified, and an optimum site for screw placement is determined. An awl is used to breach the anterior cortex with an awl guide used to ensure that the awl is driven perpendicular to the anterior cortex. A bone screw of appropriate length is selected and then is driven into the starter hole to the proper depth using the adjustable-depth driver giving care to place the bone screw perpendicular to the anterior cortex in both the lateral and transverse planes. These steps are repeated for all vertebral bodies to be plated. A malleable template is used to determine the appropriate plate length and curvature. A buttress plate is selected which is the smallest plate which allows the elongated slot to engage the heads of the bone screws and allows the claws to engage the anterior cortex. Following plate selection, the buttress plate is positioned with the elongated slot(s) over the heads of the bone screws and lightly tamped down onto the anterior cortex. This allows the claws to engage the bone. An inner screw of corresponding length is then placed into an installed bone screw. As the tip of the inner screw advances towards the tip of the bone screw, the tip of the bone screw expands, thus increasing the purchase of the screw against the vertebral body. As the tapered threads of the inner screw advance down the shaft of the bone screw, the head of the bone screw expands. This causes the external teeth of the head of the bone screw to engage the serrations of the opposing edges of the elongated slot of the buttress plate. The final turn of the inner screw will seat the screw flush with the buttress plate and will recess the top thread of the inner screw below a lip in the shaft of the bone screw. These steps are repeated until the last inner screw is in place.

Several benefits and advantages are derived from the invention. The apparatus and method of the invention allows a physician to choose an optimum location for the first bone screw on the first vertebral body (e.g., on the first cervical vertebral body) and to choose an optimum location for the second bone screw on the second vertebral body (e.g., on the second cervical vertebral body) for maximum attachment strength and mechanical stability. This is accomplished by first installing the bone screws on the vertebral bodies and then securing the buttress plate to the installed bone screws. In comparison, the prior art forces the physician to use pre-drilled holes in the buttress plate which often provide less than optimum attachment locations (providing less attachment strength and less mechanical stability) for the bone screws to be installed in the vertebral bodies.

The foregoing description of several expressions of a preferred embodiment of the invention and several methods of the invention has been presented for purposes of illustration. It is not intended to be exhaustive or to limit the invention to the precise forms and processes disclosed, and obviously many modifications and variations are possible in light of the above teaching. It is intended that the scope of the invention be defined by the claims appended hereto.

What is claimed is:

1. A spinal-column buttress plate assembly for attaching together first and second vertebral bodies of a spinal column of a medical patient, the spinal-column buttress plate assembly comprising:

a spinal-vertebral buttress plate having first and second elongated slots, the first slot extending in a first direction that is substantially parallel to the spinal column and the second slot extending in a direction that defines an acute angle with the spinal column; and first and second bone screws configured to pass at least partially through the first and second slots.

2. A spinal-column buttress plate assembly for attaching together first and second vertebral bodies of a spinal column of a medical patient, the spinal-column buttress plate assembly comprising:

a spinal-vertebral buttress plate having first, second and third elongated slots, the first slot extending in a first direction, the second slot extending in a direction that is perpendicular to the spinal column and the third slot extending in a direction that is different than the first and second directions; and first and second bone screws configured to pass at least partially through the first and second slots.

3. A spinal-column buttress plate assembly for attaching together first and second vertebral bodies of a spinal column of a medical patient, the spinal-column buttress plate assembly comprising:

a spinal-vertebral buttress plate having first, second and third elongated slots, the first slot extending in a first direction that is substantially parallel to the spinal column, the second slot extending in a direction that has a component which is transverse to the spinal column and the third slot extending in a direction that is different than the first and second directions; and first and second bone screws configured to pass at least partially through the first and second slots.

4. A spinal-column buttress plate assembly as claimed in claim 3, wherein the third direction has a component which is transverse to the spinal column.

5. A spinal-column buttress plate assembly for attaching together first and second vertebral bodies of a spinal column of a medical patient, the spinal-column buttress plate assembly comprising:

a spinal-vertebral buttress plate defining a longitudinal axis and having first and second elongated slots, the first slot extending in a first direction and the second slot extending in a direction that is substantially perpendicular to the spinal column when the longitudinal axis is substantially parallel to spinal column; and first and second bone screws configured to pass at least partially through the first and second slots.

6. A spinal-column buttress plate assembly for attaching together first and second vertebral bodies of a spinal column of a medical patient, the spinal-column buttress plate assembly comprising:

a spinal-vertebral buttress plate defining a longitudinal axis and having first and second elongated slots, the first slot extending in a first direction that is substantially parallel when the spinal column when the longitudinal axis is substantially parallel to spinal column and the second slot extending in a direction that has a component which is transverse to the spinal column when the longitudinal axis is substantially parallel to spinal column; and first and second bone screws configured to pass at least partially through the first and second slots.

7. A spinal-column buttress plate assembly as claimed in claim 6, wherein the second slot extends in a direction that defines an acute angle with the spinal column.

8. A spinal-column buttress plate assembly, comprising:

a spinal-vertebral buttress plate defining at least one elongated slot with rough opposing edges; and first and second bone screws, each bone screw including a shaft which is insertable into the spinal column and an expandable head, associated with the shaft, with a rough surface having an unexpanded state in which the head can pass through the at least one elongated slot and an expanded state in which the head is prevented from passing through the at least one elongated slot and the rough surface of the head engages the rough opposing edges of the at least one slot.

9. A spinal-column buttress plate assembly as claimed in claim 8, wherein the at least one elongated slot includes internal teeth and the expandable head includes external teeth.

10. A spinal-column buttress plate assembly as claimed in claim 8, further comprising:

apparatus that moves the heads of the first and second bone screws from the unexpanded state to the expanded state.

11. A spinal-column buttress plate assembly as claimed in claim 8, wherein the first and second bone screws define respective threaded holes, the spinal-column buttress plate assembly further comprising:

first and second inner screws respectively configured to engage the threaded holes of the first and second bone screws and drive the expandable heads of the first and second bone screws from the unexpanded state to the expanded state.

12. A spinal-column buttress plate assembly as claimed in claim 11, wherein the first and second bone screws includes expandable tips and the first and second inner screws are configured to expand the expandable tips of the first and second bone screws.

13. A spinal-column buttress plate assembly as claimed in claim 8, wherein the first and second bone screws includes expandable tips, the spinal-column buttress plate assembly further comprising:

apparatus that expands the expandable tips.

14. A spinal-column buttress plate assembly for attaching together first and second vertebral bodies of a spinal column of a medical patient, wherein the buttress plate assembly comprises:

a) a spinal-vertebral buttress plate having an elongated slot with opposing edges and claws engageable with the first and second vertebral bodies;

b) a first screw assembly including:
(1) a first inner screw,
(2) a first bone screw having an internally-threaded hole, having a shaft which is insertable into the first vertebral body of the spinal column of the medical patient, having an expandable head, with a substantially rectangular shape, which is attached to the shaft of the first bone screw and which has a first unexpanded state and a first expanded state, wherein the head of the first bone screw is small enough to pass through the elongated slot in the first unexpanded state but not in the first expanded state, and having first means for trapping the first inner screw when the first inner screw is fully engaged in the internally-threaded hole of the first bone screw; and and c) a second screw assembly including:
(1) a second inner screw,
(2) a second bone screw having an internally-threaded hole, having a shaft which is insertable into the second vertebral body of the spinal column of the medical patient, having an expandable head, with a substantially rectangular shape, which is attached to the shaft of the second bone screw and which has a second unexpanded state and a second expanded state, wherein the head of the second bone screw is small enough to pass through the elongated slot in the second unexpanded state but not in the second expanded state, and having second means for trapping the second inner screw when the second inner screw is fully engaged in the internallythreaded hole of the second bone screw; and wherein the first and second inner screws are engageable, respectively, in the internally-threaded holes of the first and second bone screws to expand the heads of the first and second bone screws to engage the heads of the first and second bone screws against the opposing edges of the elongated slot of the buttress plate after the elongated slot of the buttress plate has been disposed to enclose the heads of the first and second bone screws after the first and second bone screws have been inserted into the first and second vertebral bodies.

15. A spinal-column buttress plate assembly for attaching together first and second vertebral bodies of a spinal column of a medical patient, the buttress plate assembly comprising:

a) a spinal-vertebral buttress plate having first and second elongated slots each with opposing edges, at least one of the slots extending in a direction that has a component which is transverse to the spinal column;

b) a first screw assembly including:
(1) a first bone screw having an internally-threaded hole, having a shaft which is insertable into the first vertebral body of the spinal column of the medical patient, and having an expandable head which is attached to the shaft of the first bone screw and which has a first unexpanded state and a first expanded state, wherein the head of the first bone screw is small enough to pass through the first elongated slot in the first unexpanded state but not in the first expanded state; and
(2) a first inner screw; and c) a second screw assembly including:

(1) a second bone screw having an internally-threaded hole, having a shaft which is insertable into the second vertebral body of the spinal column of the medical patient, and having an expandable head which is attached to the shaft of the second bone screw and which has a second unexpanded state and a second expanded state, wherein the head of the second bone screw is small enough to pass through the second elongated slot in the second unexpanded state but not in the second expanded state; and (2) a second inner screw, wherein the first and second inner screws are engageable, respectively, in the internally-threaded holes of the first and second bone screws to expand the heads of the first and second bone screws to engage the heads of the first and second bone screws against the opposing edges of the first and second elongated slots of the buttress plate after the first and second elongated slots of the buttress plate have been disposed to enclose the heads of the first and second bone screws after the first and second bone screws have been inserted into the first and second vertebral bodies.

16. A cervical-column buttress plate assembly for fusing together first and second cervical vertebral bodies of a cervical column of a medical patient, wherein the buttress plate assembly comprises:

a) a cervical-vertebral buttress plate having an elongated slot with opposing and serrated edges;

b) a first screw assembly including:

(1) a first bone screw having an internally-threaded hole, having an externally-threaded shaft which is threadably insertable into the first cervical vertebral body of the cervical column of the medical patient and which has an expandable tip, and having an expandable head which is attached to the shaft of the first bone screw and which has external teeth; and (2) a first inner screw; and c) a second screw assembly including:

(1) a second bone screw having an internally-threaded hole, having an externally-threaded shaft which is threadably insertable into the second cervical vertebral body of the cervical column of the medical patient and which has an expandable tip, and having an expandable head which is attached to the shaft of the second bone screw and which has external teeth; and (2) a second inner screw, wherein the first and second inner screws are engageable, respectively, in the internally-threaded holes of the first and second bone screws to expand the tips of the first and second bone screws against the first and second cervical vertebral bodies and to expand the heads of the first and second bone screws to engage the external teeth of the heads of the first and second bone screws against the opposing and serrated edges of the elongated slot of the buttress plate after the elongated slot of the buttress plate has been disposed to enclose the heads of the first and second bone screws after the first and second bone screws have been threadably inserted into the first and second vertebral bodies.

17. The spinal-column buttress plate assembly of claim 16, wherein the buttress plate includes claws engageable with the first and second cervical vertebral bodies.

18. The spinal-column buttress plate assembly of claim 16, wherein the first bone screw includes first means for trapping the first inner screw when the first inner screw is fully engaged in the internally-threaded hole of the first bone screw, and wherein the second bone screw includes second means for trapping the second inner screw when the second inner screw is fully engaged in the internally-threaded hole of the second bone screw.

19. The spinal-column buttress plate assembly of claim 16, wherein the head of the first bone screw has a substantially rectangular shape, and wherein the head of the second bone screw has a substantially rectangular shape.

20. The spinal-column buttress plate assembly of claim 16, wherein the buttress plate includes claws engageable with the first and second cervical vertebral bodies, wherein the first bone screw includes first means for trapping the first inner screw when the first inner screw is fully engaged in the internally-threaded hole of the first bone screw, wherein the second bone screw includes second means for trapping the second inner screw when the second inner screw is fully engaged in the internally-threaded hole of the second bone screw, wherein the head of the first bone screw has a substantially rectangular shape, and wherein the head of the second bone screw has a substantially rectangular shape.

21. A spinal-column buttress plate assembly for attaching together first and second vertebral bodies of a spinal column of a medical patient, wherein the buttress plate assembly comprises:

a) a spinal-vertebral buttress plate having an elongated slot with opposing edges;

b) a first screw assembly including:

(1) a first bone screw having an internally-threaded hole, having a shaft which is insertable into the first vertebral body of the spinal column of the medical patient, and having an expandable head, with a substantially rectangular shape, which is attached to the shaft of the first bone screw and which has a first unexpanded state and a first expanded state, wherein the head of the first bone screw is small enough to pass through the elongated slot in the first unexpanded state but not in the first expanded state, and (2) a first inner screw; and c) a second screw assembly including:

(1) a second bone screw having an internally-threaded hole, having a shaft which is insertable into the second vertebral body of the spinal column of the medical patient, and having an expandable head, with a substantially rectangular shape, which is attached to the shaft of the second bone screw and which has a second unexpanded state and a second expanded state, wherein the head of the second bone screw is small enough to pass through the elongated slot in the second unexpanded state but not in the second expanded state, and (2) a second inner screw;

wherein the first and second inner screws are engageable, respectively, in the internally-threaded holes of the first and second bone screws to expand the heads of the first and second bone screws to engage the heads of the first and second bone screws against the opposing edges of the elongated slot of the buttress plate after the elongated slot of the buttress plate has been disposed to enclose the heads of the first and second bone screws after the first and second bone screws have been inserted into the first and second vertebral bodies.

22. A spinal-column buttress plate assembly for attaching together first and second vertebral bodies of a spinal column of a medical patient, the buttress plate assembly comprising:

a) a spinal-vertebral buttress plate having an elongated slot with opposing edges;

b) a first screw assembly including:
   (1) a first inner screw, and
   (2) a first bone screw having an internally-threaded hole, having a shaft which is insertable into the first vertebral body of the spinal column of the medical patient, having an expandable head which is attached to the shaft of the first bone screw and which has a first unexpanded state and a first expanded state, wherein the head of the first bone screw is small enough to pass through the elongated slot in the first unexpanded state but not in the first expanded state and having first means for trapping the first inner screw when the first inner screw is fully engaged in the internally-threaded hole of the first bone screw; and c) a second screw assembly including:
   (1) a second inner screw, and
   (2) a second bone screw having an internally-threaded hole, having a shaft which is insertable into the second vertebral body of the spinal column of the medical patient, having an expandable head which is attached to the shaft of the second bone screw and which has a second unexpanded state and a second expanded state, wherein the head of the second bone screw is small enough to pass through the elongated slot in the second unexpanded state but not in the second expanded state and having second means for trapping the second inner screw when the second inner screw is fully engaged in the internally-threaded hole of the second bone screw;

wherein the first and second inner screws are engageable, respectively, in the internally-threaded holes of the first and second bone screws to expand the heads of the first and second bone screws to engage the heads of the first and second bone screws against the opposing edges of the elongated slot of the buttress plate after the elongated slot of the buttress plate has been disposed to enclose the heads of the first and second bone screws after the first and second bone screws have been inserted into the first and second vertebral bodies.

23. A spinal-column buttress plate assembly for attaching together first and second vertebral bodies of a spinal column of a medical patient, each of the first and second vertebral bodies defining a mid-point along the longitudinal axis defined by the spinal column, the buttress plate assembly comprising:

a) a spinal-vertebral buttress plate having an elongated slot with opposing edges that defines a length sufficient to extend from the mid-point of the first vertebral body to the mid-point of the second vertebral body;

b) a first screw assembly including:
   (1) a first bone screw having an internally-threaded hole, having a shaft which is insertable into the first vertebral body of the spinal column of the medical patient, and having an expandable head which is attached to the shaft of the first bone screw and which has a first unexpanded state and a first expanded state, wherein the head of the first bone screw is small enough to pass through the elongated slot and move along its length in the first unexpanded state but not in the first expanded state; and
   (2) a first inner screw; and c) a second screw assembly including:
   (1) a second bone screw having an internally-threaded hole, having a shaft which is insertable into the second vertebral body of the spinal column of the medical patient, and having an expandable head which is attached to the shaft of the second bone screw and which has a second unexpanded state and a second expanded state, wherein the head of the second bone screw is small enough to pass through the elongated slot in the second unexpanded state and move along its length but not in the second expanded state; and
   (2) a second inner screw, wherein the first and second inner screws are engageable, respectively, in the internally-threaded holes of the first and second bone screws to expand the heads of the first and second bone screws to engage the heads of the first and second bone screws against the opposing edges of the elongated slot of the buttress plate after the elongated slot of the buttress plate has been disposed to enclose the heads of the first and second bone screws after the first and second bone screws have been inserted into the first and second vertebral bodies.

24. The spinal-column buttress plate assembly of claim 23, wherein the buttress plate includes claws engageable with the first and second vertebral bodies.

25. A method for attaching together first and second vertebral bodies of a spinal column of a medical patient, the method comprising the steps of:

a) obtaining first and second bone screws;

b) obtaining a buttress plate having first and second slots with opposing edges;

c) inserting the first bone screw into the first vertebral body of the spinal column of the medical patient;

d) inserting the second bone screw into the second vertebral body of the spinal column of the medical patient; and e) attaching the buttress plate to the first and second bone screws after performing steps a) through d) by expanding respective portions of the first and second bone screws into engagement with the opposing edges of the first and second slots.

26. A method for attaching together first and second vertebral bodies of a spinal column of a medical patient, wherein the method comprises the steps of:

a) obtaining first and second bone screws each having an internally-threaded hole, each having a shaft, and each having an expandable head attached to a corresponding shaft, b) obtaining first and second inner screws engage able, respectively, with the internally-threaded holes of the first and second bone screws to expand the heads of the first and second bone screws;

c) obtaining a buttress plate having an elongated slot with opposing edges;

d) inserting the first bone screw into the first vertebral body of the spinal column of the medical patient with the head of the first bone screw protruding above the first vertebral body;

e) inserting the second bone screw into the second vertebral body of the spinal column of the medical patient with the head of the second bone screw protruding above the second vertebral body;

f) placing the buttress plate on the first and second vertebral bodies with the heads of the first and second bone screws disposed in the elongated slot of the buttress plate;

g) threading the first inner screw into the internally-threaded hole of the first bone screw expanding the head of the first bone screw to engage the head of the first bone screw against the opposing edges of the elongated slot of the buttress plate; and h) threading the second inner screw into the internally-threaded hole of the second bone screw expanding the head of the second bone screw to engage the head of the second bone screw against the opposing edges of the elongated slot of the buttress plate.

27. The method of claim 26, wherein the first and second vertebral bodies of the spinal column are adjacent first and second vertebral bodies of the spinal column.

28. The method of claim 27, wherein step d) inserts the first bone screw into the anterior cortex of the first vertebral body, and wherein step e) inserts the second bone screw into the anterior cortex of the second vertebral body.

29. The method of claim 28, wherein step d) inserts the first bone screw into the first vertebral body along the midline of the first vertebral body, and wherein step e) inserts the second bone screw into the second vertebral body along the midline of the second vertebral body.

30. The method of claim 29, wherein the buttress plate has claws, and wherein step f) includes tamping down the buttress plate to engage the claws into the anterior cortex of the first and second vertebral bodies.

31. A method for attaching together first and second vertebral bodies of a spinal column of a medical patient, wherein the method comprises the steps of:

a) obtaining first and second bone screws each having an internally-threaded hole, each having a shaft, and each having an expandable head attached to the shaft, b) obtaining first and second inner screws engage able, respectively, with the internally-threaded holes of the first and second bone screws to expand the heads of the first and second bone screws;

c) obtaining a buttress plate having first and second elongated slots each with opposing edges;

d) inserting the first bone screw into the first vertebral body of the spinal column of the medical patient with the head of the first bone screw protruding above the first vertebral body;

e) inserting the second bone screw into the second vertebral body of the spinal column of the medical patient with the head of the second bone screw protruding above the second vertebral body;

f) placing the buttress plate on the first and second vertebral bodies with the head of the first bone screw disposed in the first elongated slot of the buttress plate and with the head of the second bone screw disposed in the second elongated slot of the buttress plate;

g) threading the first inner screw into the internally-threaded hole of the first bone screw expanding the head of the first bone screw to engage the head of the first bone screw against the opposing edges of the elongated slot of the buttress plate; and h) threading the second inner screw into the internally-threaded hole of the second bone screw expanding the head of the second bone screw to engage the head of the second bone screw against the opposing edges of the elongated slot of the buttress plate.

32. A method for fusing together first and second vertebral bodies of a spinal column of a medical patient, wherein the method comprises the steps of:

a) obtaining first and second bone screws each having an internally-threaded hole, each having a shaft with an expandable tip, and each having an expandable head attached to a corresponding shaft and having external teeth, b) obtaining first and second inner screws engageable, respectively, with the internally-threaded holes of the first and second bone screws to expand the tips and the heads of the first and second bone screws;

c) obtaining a buttress plate having an elongated slot with opposing and serrated edges;

d) inserting the first bone screw into the first vertebral body of the spinal column of the medical patient with the head of the first bone screw protruding above the first vertebral body;

e) inserting the second bone screw into the second vertebral body of the spinal column of the medical patient with the head of the second bone screw protruding above the second vertebral body;

f) placing the buttress plate on the first and second vertebral bodies with the heads of the first and second bone screws disposed in the elongated slot of the buttress plate;

g) threading the first inner screw into the internally-threaded hole of the first bone screw expanding the tip of the first bone screw against the first vertebral body and expanding the head of the first bone screw to engage the external teeth of the head of the first bone screw against the opposing and serrated edges of the elongated slot of the buttress plate; and h) threading the second inner screw into the internally-threaded hole of the second bone screw expanding the tip of the second bone screw against the second vertebral body and expanding the head of the second bone screw to engage the external teeth of the head of the second bone screw against the opposing and serrated edges of the elongated slot of the buttress plate.

33. The method of claim 32, wherein the first and second vertebral bodies of the spinal column are adjacent first and second cervical vertebral bodies of the spinal column.

34. The method of claim 33, wherein step d) inserts the first bone screw into the anterior cortex of the first cervical vertebral body, and wherein the step e) inserts the second bone screw into the anterior cortex of the second cervical vertebral body.

35. The method of claim 34, wherein step d) inserts the first bone screw into the first cervical vertebral body along the midline of the first cervical vertebral body, and wherein step e) inserts the second bone screw into the second cervical vertebral body alone the midline of the second cervical vertebral body.

36. The method of claim 36, wherein the buttress plate has claws, and wherein step f) includes tamping down the buttress plate to engage the claws into the anterior cortex of the first and second cervical vertebral bodies.

* * * * *